US012702372B2

(12) United States Patent
Tsai et al.

(10) Patent No.: US 12,702,372 B2
(45) Date of Patent: Aug. 11, 2026

(54) MULTI-VIEW EXPOSURE X-RAY IMAGE POSITIONING METHOD AND SYSTEM

(71) Applicant: SHANGHAI TAOIMAGE MEDICAL TECHNOLOGY CO., LTD., Shanghai (CN)

(72) Inventors: Tsungyuan Tsai, Shanghai (CN); Cong Wang, Shanghai (CN)

(73) Assignee: SHANGHAI TAOIMAGE MEDICAL TECHNOLOGY CO., LTD., Shanghai (CN)

( * ) Notice: Subject to any disclaimer, the term of this patent is extended or adjusted under 35 U.S.C. 154(b) by 156 days.

(21) Appl. No.: 18/847,555

(22) PCT Filed: Jul. 29, 2022

(86) PCT No.: PCT/CN2022/108820

§ 371 (c)(1),
(2) Date: Sep. 16, 2024

(87) PCT Pub. No.: WO2023/173650

PCT Pub. Date: Sep. 21, 2023

(65) Prior Publication Data

US 2025/0204878 A1 Jun. 26, 2025

(30) Foreign Application Priority Data

Mar. 18, 2022 (CN) ......................... 202210267556.1

(51) Int. Cl.

*A61B 6/50* (2024.01)
*A61B 6/00* (2006.01)
*A61B 6/40* (2024.01)

(52) U.S. Cl.

CPC ............ *A61B 6/505* (2013.01); *A61B 6/4014* (2013.01); *A61B 6/5205* (2013.01)

(58) Field of Classification Search

CPC ..... A61B 6/505; A61B 6/4014; A61B 6/5205; A61B 6/02; A61B 6/486; A61B 6/542; A61B 6/48

See application file for complete search history.

(56) References Cited

U.S. PATENT DOCUMENTS

2010/0098316 A1* 4/2010 Papaioannou ......... A61B 6/022 378/197

* cited by examiner

*Primary Examiner* — Kiho Kim

(74) *Attorney, Agent, or Firm* — MUNCY, GEISSLER, OLDS & LOWE, P.C.

(57) ABSTRACT

The present invention provides a multi-view exposure X-ray image positioning method and system, wherein the method specifically comprises: acquiring volumetric data information about a target object; shooting X-ray images corresponding to multiple view angles according to a time sequence based on a pre-set time period; and realizing position positioning of single-view-angle images according to a first optimization algorithm; in the case where the target object is in a non-static state, receiving a second image sequence according to the time sequence and performing auxiliary optimization based on different view angle images in a first pre-set time period before and after receiving the second image sequence, so as to realize position and posture optimization in a depth direction of the target object, eliminating an error of tracking and positioning only in one view angle, and realizing accurate positioning of the target object in a dynamic time sequence image.

10 Claims, 5 Drawing Sheets

MULTI-VIEW EXPOSURE X-RAY IMAGE POSITIONING METHOD AND SYSTEM

TECHNICAL FIELD

The present invention relates to the field of image processing, and more particularly, to a multi-view exposure X-ray image positioning method and system.

BACKGROUND ART

At present, X-ray is commonly used in clinical and scientific research to quantify the motion state of bone joints. However, in the process of bone joint motion, the spatial position information using single-view X-ray images often results in out-of-plane motion positioning error. Therefore, in the prior art, multi-view dynamic X-ray images are mostly used to accurately position the bone joints. However, currently, in a multi-view image tracking environment composed of multiple C-arm machines, the X-ray emission time thereof cannot be determined. There must be a time sequence for the actual imaging exposure time of the same target. That is to say, the target objects photographed at different view angles are not target objects photographed at the same time, and simply taking multiple dynamic X-ray imaging devices of the same specification as synchronous imaging often results in difficulty in achieving convergence on automatic registration.

In the prior art, there is an error in depth calculation due to tracking positioning using only one view angle, resulting in a calculated position that is not close to the true position. Therefore, it is necessary to use images with other view angles to overcome the positioning error caused by the single view angle.

SUMMARY OF THE INVENTION

The present invention is based on a multi-view exposure X-ray image positioning method and system. The accurate positioning of a target object in dynamic time sequence images is achieved by positioning position information about the target object by a first optimization algorithm at different view angles, and then positioning position information about the target object at each view angle by a second optimization algorithm. The present invention specifically comprises the contents below.

In a first aspect, the present invention provides a multi-view exposure X-ray image positioning method. The arranging a plurality of X-ray generators and a plurality of receiving plates at relative positions among different shooting view angles comprises: acquiring volumetric data information about a target object;

- according to the volumetric data information, sequentially shooting X-ray images corresponding to multiple view angles according to a time sequence based on a pre-set time period;
- in the case where the target object is in a static state, receiving the X-ray images of all view angles at a moment corresponding to the static state to generate a first image sequence, and obtaining a first rotation displacement matrix according to a first optimization algorithm;
- in the case where the target object is in a non-static state, sequentially receiving the X-ray images from a first view angle to a last view angle in the pre-set time period as a second image sequence according to the time sequence, and processing the second image sequence to obtain second rotation matrices; and
- achieving dynamic positioning of the X-ray image of the target object according to the first rotation displacement matrix, and the plurality of second rotation matrices corresponding to the image sequences in the non-static state.

In a possible implementation of the present application, a plurality of X-ray generators and a plurality of receiving plates are arranged at relative positions among different shooting view angles; and the relative positions among the different shooting view angles are the relative positions of the transmitting sources of the X-ray generators of and the receiving plates different groups, and the X-ray images of multiple view angles are obtained by shooting with the X-ray generators and the receiving plates of different groups.

In a possible implementation of the present application, the case where the target object is in the static state comprises that the target object is in a scanning start period or a scanning end period, respectively.

In a possible implementation of the present application, the processing the second image sequence to obtain the second rotation displacement matrix comprises:

- in the case where the receiving of the second image sequence is completed, generating a secondary rotation displacement matrix corresponding to each view angle in the pre-set time period according to the first optimization algorithm; and
- updating the secondary rotation displacement matrix in the pre-set time period by the second optimization algorithm to obtain the corresponding second rotation displacement matrix.

In a possible implementation of the present application, the first optimization algorithm comprises:

- Step 110, presetting a first position where a target object projection approaches to a real image of the target object along a projection direction from a transmitting source to a receiving plate, and calculating a first similarity $S_1$ between the target object projection and the real image $X^{view\_1}$;
- Step 210, selecting a second position, generating a matrix $T_{first}$ corresponding to the second position, and re-projecting according to the second position and calculating a second similarity $S_2$; judging whether $S_1$ is less than $S_2$;
- if so, receiving the current position $T_{first}$, and proceeding to Step 310;
- if not, proceeding to Step 410;
- Step 310, setting the matrix $T_{first}$ as a matrix $T_{second}$;
- Step 410, the quantity of times of updating and calculating $T_{first}$ is acquired, and it is judged whether an iteration condition is preset;
- if so, receiving the current location $T_{first}$, and
- if not, returning to Step 210.

In a possible implementation of the present application, the updating the secondary rotation displacement matrix in the pre-set time period by the second optimization algorithm to obtain the corresponding second rotation displacement matrix comprises: Step 120, based on a position view angle corresponding to the secondary rotation displacement matrix, taking the position and posture of other view angles as a reference, calculating a matrix $T_{ave}$ corresponding to a Z-axis direction displacement and a rotation value N1 around X and Y axes;

- Step 220, fixing the Z-axis direction displacement and the rotation value N1 around the X and Y axes, selecting a second position, generating a matrix $T'_{first}$ corresponding to the second position, and re-projecting according to the second position and calculating the Z-axis direction displacement and a rotation value N2 around the X and Y axes; judging whether the similarity $S_{ave}$ generated corresponding to the $T_{ave}$ is less than a similarity $S'_{first}$ generated corresponding to the $T'_{first}$, if so, receiving the Z-axis direction displacement and the rotation value N1 around the X and Y axes, and proceeding to step 320;

if not, proceeding to Step 420;

Step 320, setting the matrix $T'_{first}$ as a matrix $T'_{final}$;

Step 420: acquiring a quantity of times of updating and calculating $T'_{first}$, and judging whether a preset iteration condition is satisfied;

if so, receiving the current location $T_{first}$, if not, returning to Step 220.

In a possible implementation of the present application, the taking the position and posture of other view angles as the reference comprises:

according to the position of the first view angle in the current first pre-set time period, acquiring an average value of the position and posture of a next view angle in the previous pre-set time period before the current first pre-set time period and the position and posture of the next view angle in the current first pre-set time period; and converting the average value into the first view angle, and replacing the Z-axis direction displacement and the rotation about X and Y axes in a detector coordinate system in the first view angle of the secondary rotation displacement matrix.

In a possible implementation of the present application, the fixing the Z-axis direction displacement and the rotation value around the X and Y axes comprises:

obtaining a matrix based on the position of the current first pre-set time period as: $T=T_{4\times4}$, ⇌ i.e., $$\begin{bmatrix} R_{3\times3} & V_{1\times3} \\ 0 & 1 \end{bmatrix},$$

where the matrix comprises six translation and rotation elements (x, y, z, γ, α, β);

where $R_{3\times3}$ is a rotation matrix $R_{\alpha\times a}=R_\gamma*R_\alpha*R_\beta$ in relation to the three axes; and $V_{1\times3}$ are translation vectors $$V_{1\times3} = \begin{bmatrix} x \\ y \\ z \end{bmatrix}$$

along the three axes.

In a second aspect, the present application provides a multi-view exposure X-ray image positioning system, comprising:

a data acquisition module configured for acquiring volumetric data information about a target object;

a data collection module configured for, according to the volumetric data information, sequentially shooting X-ray images corresponding to multiple view angles according to a time sequence based on a pre-set time period;

a first data receiving module configured for, in the case where the target object is in a static state, receiving the X-ray images of all view angles at a moment corresponding to the static state to generate a first image sequence, and obtaining a first rotation displacement matrix according to a first optimization algorithm;

a second data receiving module configured for, in the case where the target object is in a non-static state, receiving the X-ray images from a first view angle to a last view angle in the pre-set time period as a second image sequence according to the time sequence, and performing optimization processing on the second image sequence to obtain second rotation displacement matrices; and a positioning module configured for achieving dynamic positioning of the X-ray image of the target object according to the first rotation displacement matrix, and the plurality of second rotation matrices corresponding to the image sequences in the non-static state. In particular, the second data receiving module further comprises:

a first optimization unit of second data configured for, in the case where the receiving of the second image sequence is completed, generating a secondary rotation displacement matrix corresponding to the pre-set time period based on the first optimization algorithm; and a second optimization unit of second data configured for updating the secondary rotation displacement matrix in the pre-set time period by the second optimization algorithm to obtain the corresponding second rotation displacement matrix.

The invention has the following beneficial effects compared to prior art.

In the present invention, by setting a plurality of multi-view angles to expose X-ray images, based on the fact that the actual imaging exposure time of the same target object must have a time sequence during the imaging of actual X-ray images. It is achieved without setting a plurality of dynamic X-ray imaging devices of the same specification to be synchronized. Namely, in the case where the target objects shot at a plurality of different view angles are not target objects at the same moment. The position information thereof at different view angles is respectively optimized based on different view angles according to the first optimization algorithm. At the same time, in the case where the target object is in a non-static state, the position information of each view angle is optimized on the basis of time sequence by the second optimization algorithm. The error of depth calculation is compensated by collecting the images of the moments before and after from adjacent view angles in the current pre-set period to eliminate the error of tracking and positioning in only one view angle, so as to realize the position and posture optimization in the depth direction of the target object, and finally realize the accurate positioning of the target object in the dynamic time sequence images.

DETAILED DESCRIPTION OF THE INVENTION

Figure 1:
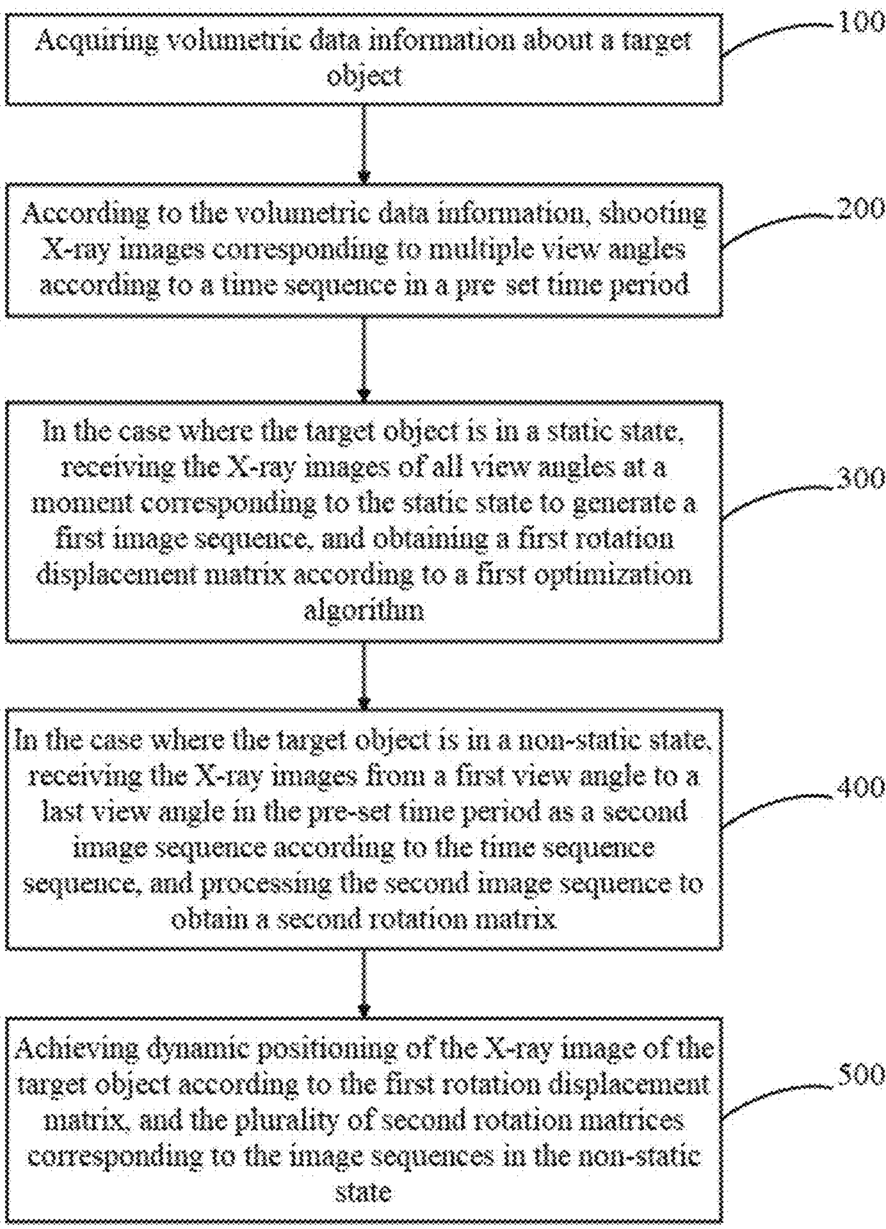
FIG. 1 shows a flow diagram of a multi-view shooting positioning according to an embodiment of the present application.

Unless defined otherwise, technical or scientific terms used in the description and claims shall have the ordinary meaning as understood by one of ordinary skill in the art to which this invention belongs.

In the description of the present invention, it should be understood that the directional or positional relationships indicated by the terms "center", "longitudinal", "horizontal", "up", "down", "front", "back", "left", "right" and "vertical", "level", "top", "bottom", "inside", "outside", "side" and the like are based on the directional or positional relationships shown in the drawings. It is merely for the purpose of describing the present application and simplifying the description, and is not intended to indicate or imply that a particular orientation, configuration and operation of the referenced device or element is required and should not be construed as limiting the scope of the present invention.

Furthermore, the terms "first", "second" and so on are used for descriptive purposes only and are not to be construed as indicating or implying relative importance or implicitly indicating the number of technical features indicated. Thus, a feature defined by "first", "second" and so on may explicitly or implicitly include one or more such features. In the description of the invention, unless otherwise specified, the meaning of "a plurality" is two or more.

The invention will now be described in detail, by way of embodiment, with reference to the accompanying drawings. It should be noted that in the specific description of these embodiments, in order to provide a concise description, it is impossible for this description to provide a detailed description of all features of the actual implementations.

As shown in FIG. 1, this embodiment provides a flow diagram of a multi-view shooting positioning. It specifically comprises the following steps.

Step 100: volumetric data information of a target object is acquired. It is understood that volumetric data information of the targeted joint includes, but not limited to, computed tomography (CT), magnetic resonance imaging (MR), three-dimensional surface models, etc. The volumetric data information is used to acquire the static three-dimensional geometric structure characteristics of the target joint or contain the internal bone texture information at the same time. The volumetric data information is irrelevant to multi-view shooting, and as the necessary preliminary data before tracking, as long as the conditions of the same target object are satisfied. It may be a bone joint, etc. and is not limited herein.

Step 200, according to the volumetric data information, X-ray images corresponding to multiple view angles are sequentially shot according to a time sequence based on a pre-set time period. It can be understood that, in the case of shooting the same target object, the target object is set to be able to be shot by X-rays at different moments in different view angles to have different X-ray images corresponding to the same pre-set time period. X-ray image shooting based on different positions can be realized by the change of the angle of the target object, so that information about the target object at different view angles is collected to realize accurate positioning of the target object at a spatial position.

In the above-mentioned step 200, a plurality of X-ray generators and a plurality of receiving plates are arranged at relative positions among different shooting view angles. The relative positions among the different shooting view angles are the relative positions of the transmitting sources of the X-ray generators and the receiving plates of different groups. The X-ray images of multiple view angles are obtained by shooting with the X-ray generators and the receiving plates of different groups It can be understood that the quantity and position of the X-ray generators and the receiving plates are in a spatial relative relationship, wherein each receiving plate receives the light rays emitted by the X-ray generator corresponding to the position thereof. During the same pre-set time period, each receiving plate receives an X-ray image of one view angle, and the images at various view angles may not be received at the same time.

Figure 2:
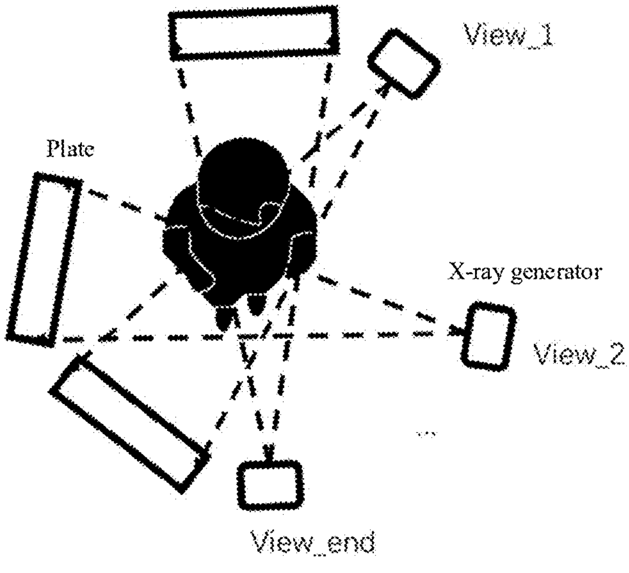
FIG. 2 shows a schematic diagram of acquiring X-ray image sequence by a multi-view shooting according to an embodiment of the present application.

In some embodiments of the present application, as shown in FIG. 2, FIG. 2 shows a schematic diagram of acquiring an X-ray image sequence by a multi-view shooting. Specifically, under the multi-view imaging system, taking the automatic registration and positioning of the target object as an example, firstly, X-ray images and CT volumetric data of the imaging area of the target object need to be acquired. In this process, the imaging area of the target object may be shot by using two C-arm X-ray machines, so as to obtain multi-view synchronous dynamic X-ray images by using a plurality of X-ray generators and receiving plates, wherein there are a plurality of receiving plates shot at multiple angles in space, so as to obtain X-ray images at multiple different shooting view angles.

According to the time range of the pre-set time period, the X-ray generators and the receiving plates are set to realize the shooting of all the view angles, so that each group of X-ray images is shot in the same time period after the respective X-ray machines are started. The dynamic shooting may be continuous shooting of multiple X-ray images to obtain image sequence data information about the target object.

Multi-view X-ray images of a target object and an image sequence ($X^{view\_1}, X^{view\_2}, \ldots, X^{view\_end}$) are shot by using several sets of X-ray generators and receiving plates, and the time information ($t^{view\_1}, t^{view\_2}, \ldots, t^{view\_end}$) about images at each view angle is acquired. With regard to devices with the same shooting rate and specification, the images thereof may be divided into image groups under different time periods, i.e., $\{X_{t\_0}, X_1, \ldots . X_{t\_1}, \ldots, X_{t\_end}\}$, wherein an $i^{th}$ group of images for a pre-set time period comprises $$\left(X_{t\_i}^{view\_1}, X_{t\_i}^{view\_2}, \ldots, X_{t\_i}^{view\_end}\right),$$

i.e., images generated by receiving plates from a view angle 1 to a view angle end shot at different moments during an $i^{th}$ time period; and view_1 to view_end are arranged in a shooting sequence within each time period.

Specifically, the pre-set time period of $X_{t\_0}$ is at a scanning initial time period, where the target object is in a static state during the pre-set time period, and the X-ray image shot at this time is a position location at the initial moment of the target object.

Specifically, the pre-set time period of $X_{t\_end}$ is at the scanning end time period, where the target object is in a static state during the pre-set time period, and the X-ray image shot at this moment is the position location at the end moment of target object.

Specifically, for any predetermined time period of $X_1, \ldots X_{t\_1}, \ldots, X_{t_{end}-1}$, the target object is in a non-static state, and the target object may rotate or move along various angles of the X-ray image system.

Step 300, in the case where the target object is in a static state, the X-ray images of all view angles are received at a moment corresponding to the static state to generate a first image sequence, and a first rotation displacement matrix is obtained according to a first optimization algorithm. It is understood that, in the case where the target object is in a static state, the imaging of the target object can be achieved within the same pre-set time period, i.e., during an initial time period or an end time period, the imaging of the target object may be achieved along all view angles of the target object provided with the receiving plates to generate the first X-ray image sequence.

In some embodiments of the present application, the first image sequence comprises image sequences of an initial time period and an end time period, and the first image sequences of the initial time period t_0 and the end time period t_end are $$X_{t\_0}^{view\_1}, X_{t\_0}^{view\_2}, \ldots, X_{t\_0}^{view\_end}, X_{t\_end}^{view\_1}, X_{t\_end}^{view\_2}, \ldots, X_{t\_end}^{view\_end}$$

respectively, where the target object is in a current position and in a static state, and X-ray images of all receiving plates are collected to form the first image sequence. The rotation displacement matrix $T_{t\_0}$ and $T_{t\_end}$ at the initial moment are located by the first optimization algorithm.

Figure 3:
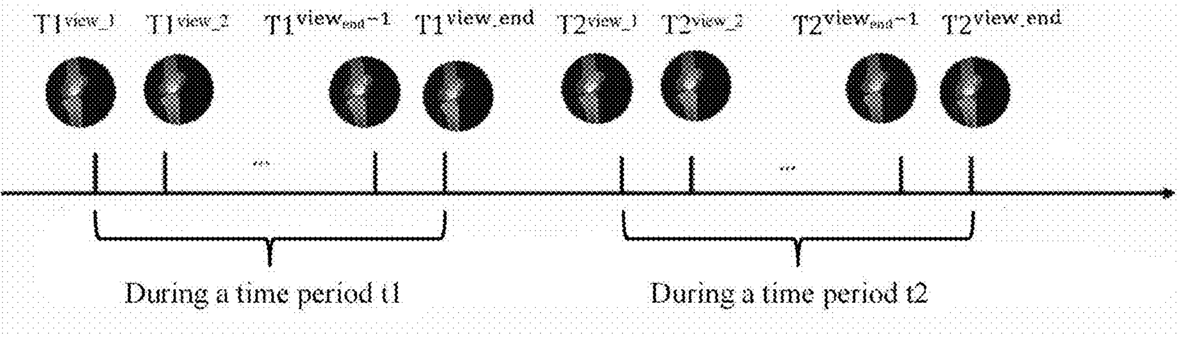
FIG. 3 shows a schematic diagram of a time sequence by a multi-view shooting according to an embodiment of the present application.

Specifically, as shown in FIG. 3, FIG. 3 shows a schematic diagram of a time sequence by a multi-view shooting. The multi-view shooting in all preset time periods corresponding to t_0 to t_end is performed in sequence according to the time sequence and shooting view angles.

In some embodiments of the present application, $T_{t\_0}$ and $T_{t\_end}$ are a 4×4 matrix, respectively, i.e., $$\begin{bmatrix} R & V \\ 0 & 1 \end{bmatrix}.$$

In the formula, R is a rotation matrix and V is a displacement matrix. Specifically, for each image sequence at any moment of $T_{t\_0}$ and $T_{t\_end}$, the rotation displacement matrix of the object needs to be finally calculated, $T=T_{4\times4}$. ⇌ i.e., $$\begin{bmatrix} R_{3\times3} & V_{1\times3} \\ 0 & 1 \end{bmatrix},$$

wherein the matrix comprises six translation and rotation elements (x, y, z, γ, α, β);

wherein $R_{3\times3}$ is a rotation matrix Ra×a=Rγ*Rα*Rβ in relation to the three axes; and $V_{1\times3}$ are translation vectors $$V_{1\times3} = \begin{bmatrix} x \\ y \\ z \end{bmatrix}$$

along the three axes.

Step 400, in the case where the target object is in a non-static state, sequentially receiving the X-ray images from a first view angle to a last view angle in the pre-set time period as a second image sequence according to the time sequence, and processing the second image sequence to obtain second rotation matrices. It can be appreciated that in the case where the target object is in a non-static state, the tracking and positioning of the target object is achieved by obtaining the dynamic target position and posture under different view angles corresponding to the pre-set time period t_2 to t_end−1.

In the above-mentioned step 400, in the case where the receiving of the second image sequence is completed, a secondary rotation displacement matrix corresponding to each view angle in the pre-set time period is generated according to the first optimization algorithm; and the secondary rotation displacement matrix in the pre-set time period is updated by the second optimization algorithm to obtain the corresponding second rotation displacement matrix. It can be understood that, with regard to the process of dynamically shooting an image sequence of the target object, the position information about the target object is obtained by using at least two optimizations. Wherein, in the first optimization process, images of one view angle $$X_{t\_i}^{view\_i}$$

are optimized. In the second optimization, the position and posture in the depth direction thereof are optimized using the images at the previous and the following moments.

Figure 4:
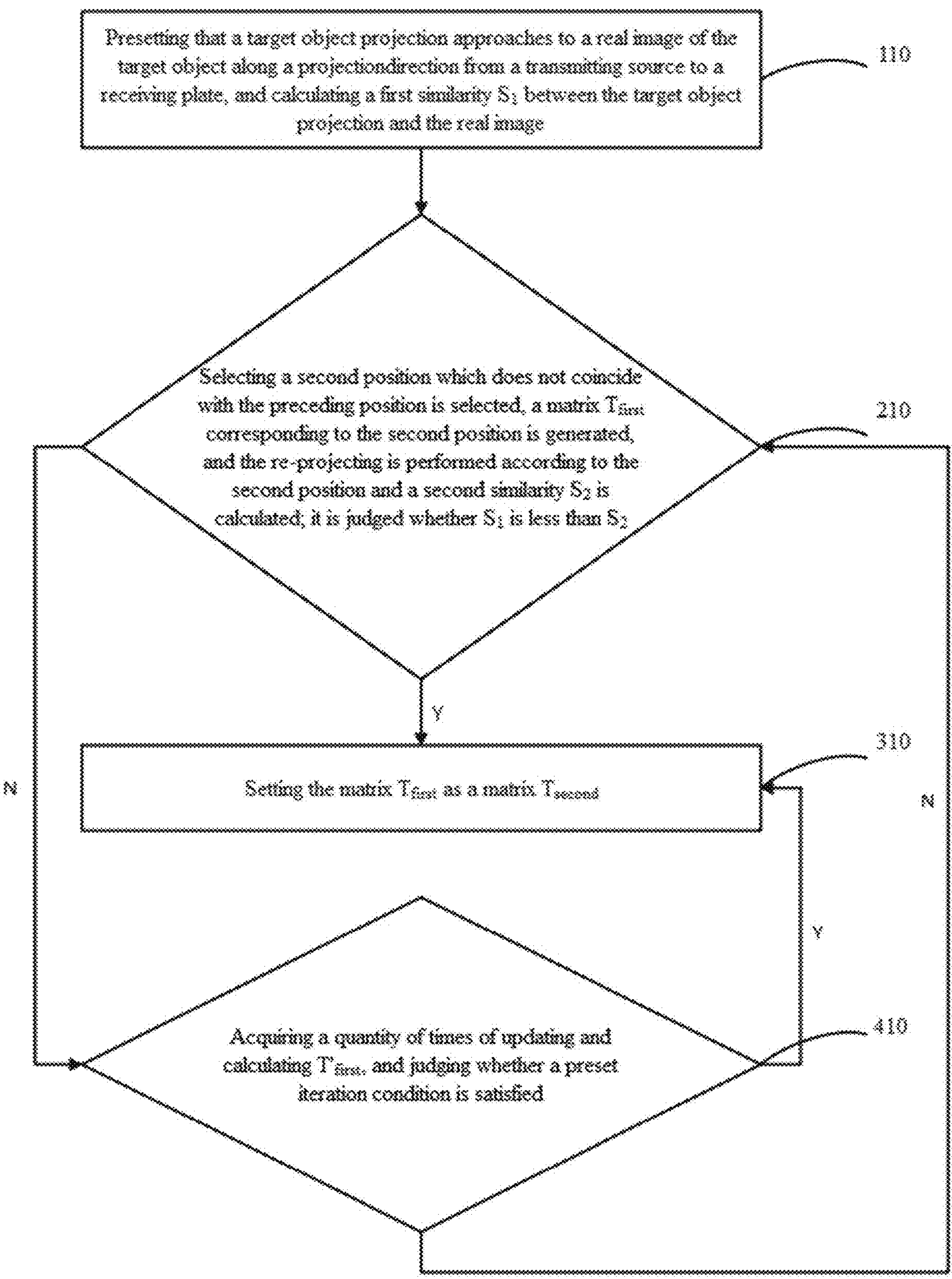
FIG. 4 shows a flow diagram of a first optimization algorithm according to an embodiment of the present application.

In a possible implementation of the present application, generating the matrix $T_{first}$ corresponding to the second position may be implemented in the simulated annealing or the particle swarm optimization algorithm implementation or other existing algorithm implementations which can implement positioning, and is not limited thereto. In some embodiments of the present application, as shown in FIG. 4, FIG. 4 shows a flow diagram of a first optimization algorithm, specifically comprising: according to the first optimization algorithm, in the case where the target object is in a static state or a non-static state, single-view X-ray image tracking is realized. When taking view1 in a pre-set time period t_i as an example, the optimization flow of the pre-set time period t_i when the target object is in a non-static state may be realized as follows.

Step 110, it presets a position that a target object moves to approach to the target position mark as a first position, so that a target object projection approaches to a real image $X^{view\_1}$ of the target object along a projection direction from a transmitting source to a receiving plate, and a first similarity $S_1$ between the target object projection and the real image $X^{view\_1}$ is calculated;

Step 210: a second position which does not coincide with the preceding position is selected, a matrix $T_{first}$ corresponding to the second position is generated, and the re-projecting is performed according to the second position and a second similarity $S_2$ is calculated; it is judged whether $S_1$ is less than $S_2$;

if so, the current position $T_{first}$ is received, and it proceeds to Step 310;

if not, it proceeds to Step 410;

Step 310, a secondary rotation displacement matrix $T_{second}$ is generated according to $T_{first}$;

Step 410, the quantity of times of recalculating $T_{\_first}$ is acquired, and it is judged whether an iteration condition is preset;

if so, the current position $T_{\_first}$ is received, and it proceeds to Step 310; and if not, it returns to Step 210.

In some embodiments of the present application, the preset iteration condition comprises conditions of being more than or equal to exceeding a pre-set calculation duration, or the similarity satisfying a pre-set similarity threshold, or the number of repeated calculations reaching a pre-set threshold, etc. which are not limited herein. The first optimization algorithm is used to realize the final $T_{first}$, namely, the displacement matrix obtained from the initial positioning under the view1 view angle within the pre-set time period of t_i.

In some embodiments of the present application, for the comparison between S1 and S2, the similarity comparison may be achieved by calculating the extracted contour coincidence degree, feature point information similarity degree, normalized mutual information, and image structure similarity degree, and is not limited thereto.

In some embodiments of the present application, the generation of several point locations is implemented based on a simulated annealing or particle swarm optimization algorithm, but the generation of locations may be implemented by other algorithms, and is not limited herein.

In the above Step 300, the generation of the $T_{t\_0}$ and $T_{t\_end}$ of the first rotation displacement matrix is performed based on the first optimization algorithm flow diagram shown in FIG. 4 when the target object is in the static state.

In the above-mentioned Step 400, the secondary rotation displacement matrix in the pre-set time period is updated by the second optimization algorithm to obtain the corresponding second rotation displacement matrix.

Figure 5:
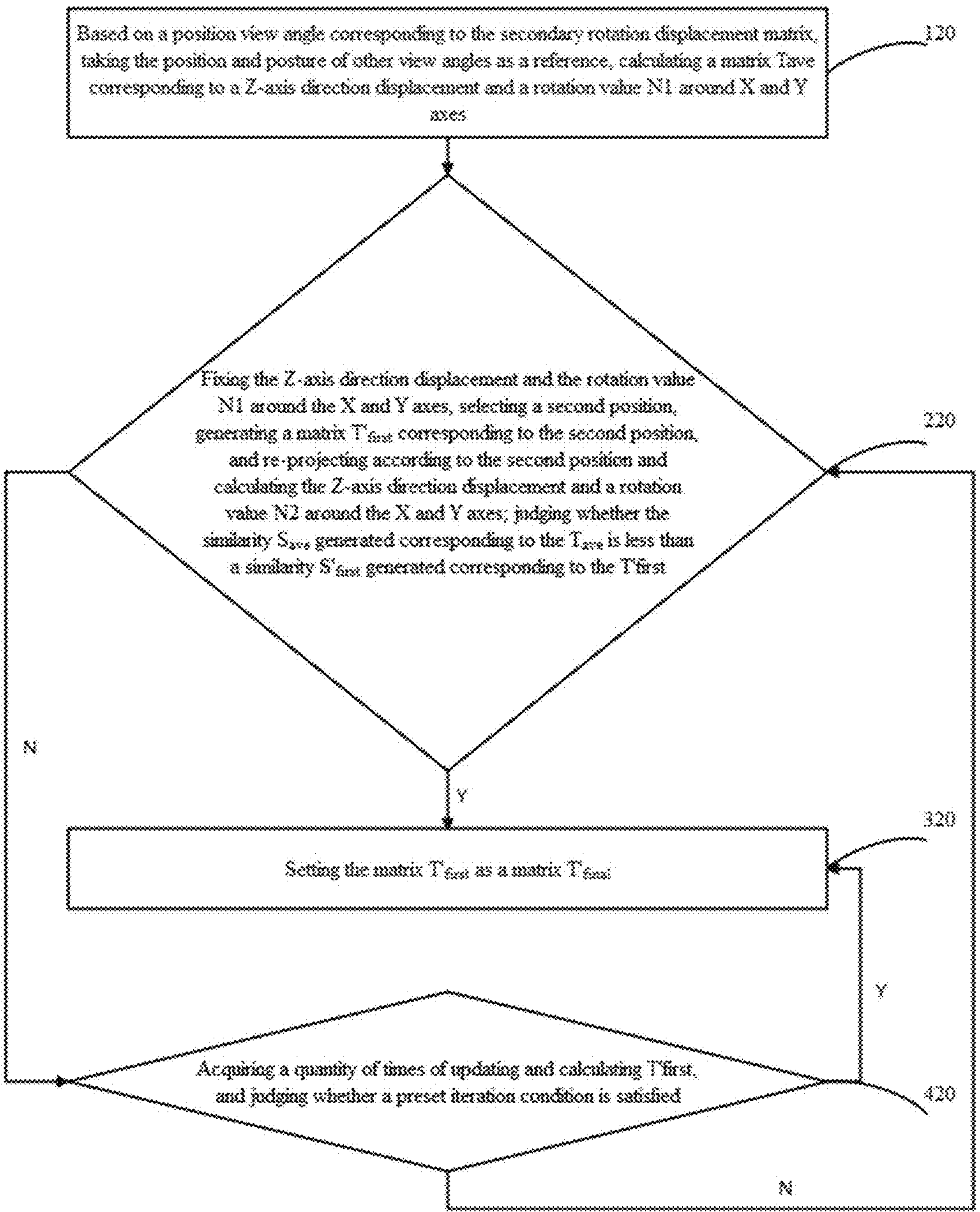
FIG. 5 shows a flow diagram of a second optimization algorithm according to an embodiment of the present application.

In particular, as shown in FIG. 5, a schematic diagram of the second optimization algorithm is shown, applicable to any view angle of any time period of the t_1 and t_end−1 pre-set periods, i.e., a schematic diagram of the positioning of the target object with the target object in the non-static state.

Step 120, based on a position view angle corresponding to the secondary rotation displacement matrix, it takes the position and posture of other view angles as a reference, and a matrix $T_{ave}$ corresponding to a Z-axis direction displacement and a rotation value N1 around X and Y axes is calculated;

Step 220: the Z-axis direction displacement and the rotation value N1 around the X and Y axes are fixed, a second position is selected, a matrix $T'_{first}$ corresponding to the second position is generated, and re-projecting is performed according to the second position and calculating the Z-axis direction displacement and a rotation value N2 around the X and Y axes; and it is judged whether the similarity $S_{ave}$ generated corresponding to the $T_{ave}$ is less than a similarity $S'_{first}$ generated corresponding to the $T'_{first}$.

if so, receiving the Z-axis direction displacement and the rotation value N1 around the X and Y axes, and proceeding to step 320;

if not, it proceeds to Step 420;

Step 320, setting the matrix $T'_{first}$ as a matrix $T'_{final}$,

Step 420: acquiring a quantity of times of updating and calculating $T'_{first}$, and judging whether a preset iteration condition is satisfied;

if so, the current position $T'_{first}$ is received, and it proceeds to Step 310;

if not, it returns to Step 220.

In some embodiments of the present application, the taking the position and posture of other view angles as the reference includes: according to the position of the first view angle in the current first pre-set time period, acquiring an average value of the position and posture of a next view angle in the previous pre-set time period before the current first pre-set time period and the position and posture of the next view angle in the current first pre-set time period; and converting the average value into the first view angle, and replacing the Z-axis direction displacement and the rotation about X and Y axes in a detector coordinate system in the first view angle of the secondary rotation displacement matrix. It can be understood that in some embodiments of the present application, with regard to an image of view_1, the average position and posture of the view angle view_2 of $$\left(T_{t_i-1}^{view\_2}, T_{t\_i}^{view\_2}\right)$$

is determined to be the position and posture at the view angle view_2, and the first optimization algorithm is re-used to iterate a rotation displacement matrix $$T_{t\_i}^{view\_1}$$

at view_1 at the fixed position and posture. With regard to view_i (wherein view_i<view_end), an average position and posture at the view_i+1 view angle of $$\left(T_{t_i-1}^{view_i+1}, T_{t\_i}^{view_i+1}\right)$$

is determined as the position and posture at the view angle view_2, and the position and posture is fixed to re-use an optimization algorithm to iterate the rotation displacement matrix $$T_{t\_i}^{view\_i}$$

at view_i. For the view angle view_end, an average position and posture at the view_1 view of $$\left(T_{t_i}^{view\_1}, T_{t_i+1}^{view\_1}\right)$$

is determined as the position and posture at view_1 view, and the position and posture is fixed to re-use a first optimization algorithm to iterate the rotation displacement matrix $$T_{t\_i}^{view\_end}$$

at view_end.

Figure 6:
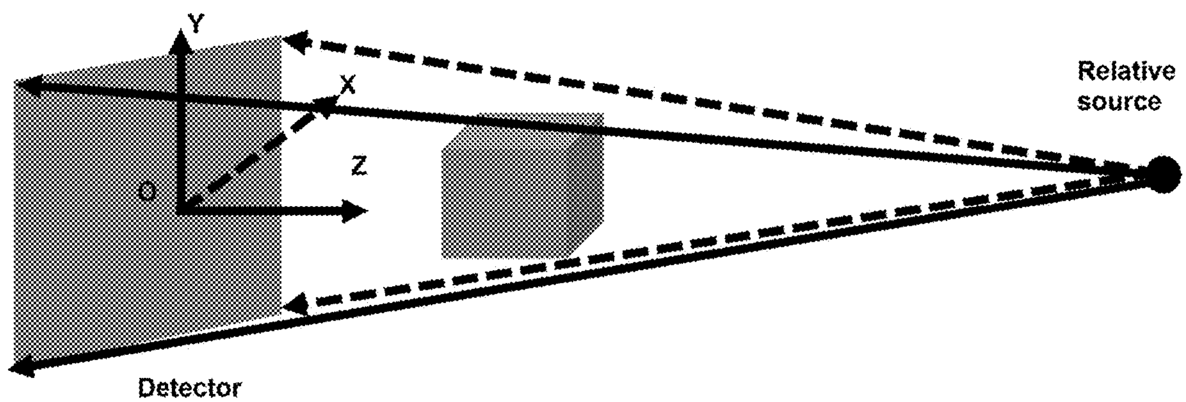
FIG. 6 shows a schematic diagram of X-ray shooting in the Z-axis direction of the detector's own coordinate system according to an embodiment of the present application.
Figure 7:
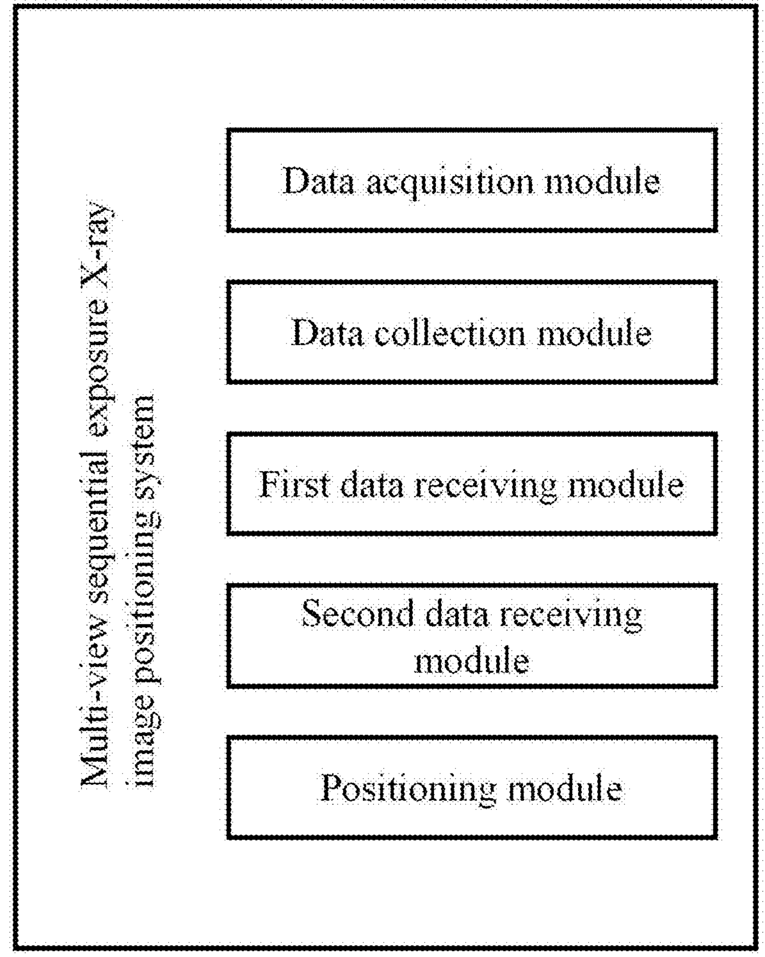
FIG. 7 shows a schematic diagram of a multi-view exposure x-ray image system according to an embodiment of the present application.

As shown in FIG. 6, FIG. 6 shows a schematic diagram of X-ray shooting in the Z-axis direction of the detector's own coordinate system according to an embodiment of the present application. Specifically, the fixing the Z-axis displacement and the rotation values about the X and Y axes include obtaining a matrix based on the position of the current first pre-set time period as: $T=T_{4\times4}$, i.e., $$T = \begin{bmatrix} R_{3\times3} & V_{1\times3} \\ 0 & 1 \end{bmatrix},$$

where the matrix comprises six translation and rotation elements (x, y, z, γ, α, β);

where $R_{3\times3}$ is a rotation matrix $R_{\alpha\times\alpha}=R\gamma*R\alpha*R\beta$ in relation to the three axes; and $V_{1\times3}$ are translation vectors $$V_{1\times3} = \begin{bmatrix} x \\ y \\ z \end{bmatrix}$$

along the three axes.

It will be appreciated that this is achieved by the second optimization algorithm to optimize the displacement along the X, Y axes and the rotation about the Z axis until a preset iteration condition is met.

Step 500, the dynamic positioning of the X-ray image of the target object is achieved according to the first rotation displacement matrix, and the plurality of second rotation matrices corresponding to the image sequences in the non-static state. It can be understood that the first rotation displacement matrix corresponds to the position information of the scanning start time period and the scanning end time period when the target object is in the static state. A plurality of second rotation matrices comprise a non-static image sequence which follows the first image sequence, and are processed according to the second image sequence to finally realize multi-sequence multi-view X-ray image positioning in the static state and the non-static state.

In some embodiments of the present application, it is also provided that a multi-view exposure X-ray image positioning system specifically comprises:

a data acquisition module configured for acquiring volumetric data information about a target object;

a data collection module configured for, according to the volumetric data information, shooting synchronous dynamic X-ray images corresponding to multiple view angles according to a time sequence in a pre-set time period;

a first data receiving module configured for, in the case where the target object is in a static state, receiving the X-ray images of all view angles at a moment corresponding to the static state to generate a first image sequence, and obtaining a first rotation displacement matrix according to a first optimization algorithm;

a second data receiving module configured for, in the case where the target object is in a non-static state, receiving the X-ray images from a first view angle to a last view angle in the pre-set time period as a second image sequence according to the time sequence, and performing optimization processing on the second image sequence to obtain second rotation displacement matrices; and a positioning module configured for achieving dynamic positioning of the X-ray image of the target object according to the first rotation displacement matrix, and the plurality of second rotation matrices corresponding to the image sequences in the non-static state. In particular, the second data receiving module further comprises:

a first optimization unit of second data configured for, in the case where the receiving of the second image sequence is completed, generating a secondary rotation displacement matrix corresponding to the pre-set time period based on the first optimization algorithm; and a second optimization unit of second data configured for updating the secondary rotation displacement matrix in the pre-set time period by the second optimization algorithm to obtain the corresponding second rotation displacement matrix.

A multi-view exposure X-ray image positioning method provided by an embodiment of the present invention is applied to a multi-view exposure X-ray image positioning system, which will not be described in detail herein.

The flowcharts and block diagram in the drawings illustrate the architecture, functionality, and operation of possible implementations of systems, methods, and computer program products according to various embodiments of the disclosure. In this regard, each block in the flowchart or block diagram may represent a module, a program segment, or part of code, which includes one or more executable instructions for implementing the specified logical functions. In some alternative implementations, the functions noted in the blocks may occur differently than the order noted in the drawings. For example, two blocks in succession may, in fact, be executed substantially concurrently or they may sometimes be executed in the reverse order, depending upon the functionality involved. It is also noted that each block of the block diagrams and/or flowcharts, and combinations of blocks in the block diagrams and/or flowcharts, can be implemented by special purpose hardware-based systems which perform the specified functions or actions, or combinations of special purpose hardware and computer instructions.

The above is only preferred implementations of the present invention, and the scope of protection of the present invention is not limited to the above-mentioned embodiments. All technical solutions falling within the concept of the present invention fall within the scope of protection of the present invention. It will be appreciated by those skilled in the art that some modifications and adaptations may be made without departing from the principle of the invention, and such modifications and alterations are intended to be included within the scope of the invention.

The invention claimed is:

1. A multi-view exposure X-ray image positioning method, wherein the method comprises:

acquiring volumetric data information about a target object;

according to the volumetric data information, sequentially shooting X-ray images corresponding to multiple view angles according to a time sequence based on a pre-set time period;

in the case where the target object is in a static state, receiving the X-ray images of all view angles at a moment corresponding to the static state to generate a first image sequence, and obtaining a first rotation displacement matrix according to a first optimization algorithm;

in the case where the target object is in a non-static state, sequentially receiving the X-ray images from a first view angle to a last view angle in the pre-set time period as a second image sequence according to the time sequence, and processing the second image sequence to obtain a plurality of second rotation matrices; and achieving dynamic positioning of the X-ray image of the target object according to the first rotation displacement matrix, and the plurality of second rotation matrices corresponding to the image sequences in the non-static state.

2. The multi-view exposure X-ray image positioning method according to claim 1, wherein before the shooting the X-ray images corresponding to multiple view angles according to the time sequence based on the pre-set time period, the method comprises:

arranging a plurality of X-ray generators and a plurality of receiving plates at relative positions among different shooting view angles; and the relative positions among the different shooting view angles are the relative positions of the transmitting sources of the X-ray generators and the receiving plates of different groups, and the X-ray images of multiple view angles are obtained by shooting with the X-ray generators and the receiving plates of different groups.

3. The multi-view exposure X-ray image positioning method according to claim 1, wherein the case where the target object is in the static state comprises that the target object is in a scanning start period or a scanning end period, respectively.

4. The multi-view exposure X-ray image positioning method according to claim 1, wherein the processing the second image sequence to obtain the second rotation displacement matrix comprises:

in the case where the receiving of the second image sequence is completed, generating a secondary rotation displacement matrix corresponding to each different view angle in the pre-set time period based on the first optimization algorithm; and updating the secondary rotation displacement matrix in the pre-set time period by the second optimization algorithm to obtain the corresponding second rotation displacement matrix.

5. The multi-view exposure X-ray image positioning method according to claim 4, wherein the updating the secondary rotation displacement matrix in the pre-set time period by the second optimization algorithm to obtain the corresponding second rotation displacement matrix comprises:

Step 120, based on a position view angle corresponding to the secondary rotation displacement matrix, taking the position and posture of other view angles as a reference, calculating a matrix $T_{ave}$ corresponding to a Z-axis direction displacement and a rotation value N1 around X and Y axes;

Step 220, fixing the Z-axis direction displacement and the rotation value N1 around the X and Y axes, selecting a second position, generating a matrix T'first corresponding to the second position, and re-projecting according to the second position and calculating the Z-axis direction displacement and a rotation value N2 around the X and Y axes; judging whether the similarity $S_{ave}$ generated corresponding to the $T_{ave}$ is less than a similarity S'first generated corresponding to the $T'_{first}$;

if so, receiving the Z-axis direction displacement and the rotation value N1 around the X and Y axes, and proceeding to step 320;

if not, proceeding to Step 420;

Step 320, setting the matrix T'first as a matrix T'final;

Step 420, acquiring a quantity of times of updating and calculating T'first, and judging whether a preset iteration condition is satisfied;

if so, receiving the current position $T'_{first}$; and if not, returning to Step 220.

6. The multi-view exposure X-ray image positioning method according to claim 5, wherein the taking the position and posture of other view angles as the reference comprises:

according to the position of the first view angle in the current first pre-set time period, acquiring an average value of the position and posture of a next view angle in the previous pre-set time period before the current first pre-set time period and the position and posture of the next view angle in the current first pre-set time period; and converting the average value into the first view angle, and replacing the Z-axis direction displacement and the rotation about X and Y axes in a detector coordinate system in the first view angle of the secondary rotation displacement matrix.

7. The multi-view exposure X-ray image positioning method according to claim 5, wherein the fixing the Z-axis direction displacement and the rotation value around the X and Y axes comprises:

obtaining a matrix based on the position of the current first pre-set time period as: $T=T_{4\times4}$, i.e., ⇌

$$\begin{bmatrix} R_{3\times3} & V_{1\times3} \\ 0 & 1 \end{bmatrix},$$

wherein the matrix comprises six translation and rotation elements (x, y, z, γ, α, β);

wherein $R_{3\times3}$ is a rotation matrix $R_{axa}=R_\gamma*R_\alpha*R_\beta$ in relation to the three axes; and $V_{1\times3}$ are translation vectors along the three axes.

8. The multi-view exposure X-ray image positioning method according to claim 1, wherein the first optimization algorithm comprises:

Step 110, presetting a first position where a target object projection approaches to a real image of the target object along a projection direction from a transmitting source to a receiving plate, and calculating a first similarity $S_1$ between the target object projection and the real image $X^{view\_1}$;

Step 210, selecting a second position, generating a matrix $T_{first}$ corresponding to the second position, and re-projecting according to the second position and calculating a second similarity $S_2$; judging whether $S_1$ is less than $S_2$;

if so, receiving the current position $T_{first}$, and proceeding to Step 310;

if not, proceeding to Step 410;

Step 310, setting the matrix $T_{first}$ as a matrix $T_{second}$;

Step 410, acquiring a quantity of times of updating and calculating $T_{first}$, and judging whether a preset iteration condition is satisfied;

if so, receiving the current location $T_{first}$; and if not, returning to Step 210.

9. A multi-view exposure X-ray image positioning system, wherein the system comprises:

a data acquisition module configured for acquiring volumetric data information about a target object;

a data collection module configured for, according to the volumetric data information, sequentially shooting X-ray images corresponding to multiple view angles according to a time sequence based on a pre-set time period;

a first data receiving module configured for, in the case where the target object is in a static state, receiving the X-ray images of all view angles at a moment corresponding to the static state to generate a first image sequence, and obtaining a first rotation displacement matrix according to a first optimization algorithm;

a second data receiving module configured for, in the case where the target object is in a non-static state, receiving the X-ray images from a first view angle to a last view angle in the pre-set time period as a second image sequence according to the time sequence, and performing optimization processing on the second image sequence to obtain a plurality of second rotation displacement matrices; and a positioning module configured for achieving dynamic positioning of the X-ray image of the target object according to the first rotation displacement matrix, and the plurality of second rotation matrices corresponding to the image sequences in the non-static state.

10. The multi-view exposure X-ray image positioning system according to claim 9, wherein the second data receiving module further comprises:

a first optimization unit of second data configured for, in the case where the receiving of the second image sequence is completed, generating a secondary rotation displacement matrix corresponding to the pre-set time period based on the first optimization algorithm; and a second optimization unit of second data configured for updating the secondary rotation displacement matrix in the pre-set time period by the second optimization algorithm to obtain the corresponding second rotation displacement matrix.

* * * * *